US00PP21367P2

(12) United States Plant Patent
Schräder

(10) Patent No.: US PP21,367 P2
(45) Date of Patent: Oct. 5, 2010

(54) **VARIETY OF *VERBENA* PLANT NAMED 'GRUELOX 01'**

(50) Latin Name: *Verbena hybridus*
Varietal Denomination: Gruelox 01

(75) Inventor: Ralf Schräder, Lüdinghausen (DE)

(73) Assignee: Grünewald Veredelings B.V., 's Gravenzande (NL)

( * ) Notice: Subject to any disclaimer, the term of this patent is extended or adjusted under 35 U.S.C. 154(b) by 0 days.

(21) Appl. No.: 12/387,010

(22) Filed: Apr. 27, 2009

(51) Int. Cl.
*A01H 5/00* (2006.01)

(52) U.S. Cl. ..... Plt./308

(58) Field of Classification Search ..... Plt./308
See application file for complete search history.

*Primary Examiner*—Annette H Para
(74) *Attorney, Agent, or Firm*—The Webb Law Firm

(57) ABSTRACT

A new and distinct *Verbena* plant named 'Gruelox 01' having plentiful flowers per spike that are light reddish-purple in color with a darker colored reddish-purple eye in the middle.

1 Drawing Sheet

Botanical classification: *Verbena hybridus.*
Varietal denomination: 'Gruelox 01'.

BACKGROUND OF THE INVENTION

The present invention comprises a new and distinct cultivar of *Verbena* plant known by the varietal name 'Gruelox 01'. The new variety was discovered in August of 2003 in a selected breeding program in Waltrop, Germany. The purpose of the breeding program was to produce a new variety of *Verbena* with large flowers and improved mildew resistance. The new variety was selected from a cross of proprietary unpatented breeding plants identified as 5-11-1 (female parent, unpatented) and 4-8 (male parent, unpatented). The new variety exhibits a bushy, compact growth habit that is similar to its parents, but exhibits more and larger flowers than both parents and also exhibits hard and glossy leaves. Further, 'Gruelox 01' has larger flowers (20 mm vs. 8-10 mm) than Verbena plant 'Sumverdi'. The new variety was first asexually reproduced in October 2003 by tipcuttings in Waltrop, Germany. The new variety has been trial and field tested and has been found to retain its distinctive characteristics and remain true to type through successive propagations.

The following traits also distinguish 'Gruelox 01' as a new and distinct cultivar from other Verbena varieties known to the breeder:

1. 'Gruelox 01' exhibits a small, purple eye;
2. 'Gruelox 01' has plentiful flowers per spike; and
3. 'Gruelox 01' has large flowers.

DESCRIPTION OF THE DRAWINGS

The accompanying photographic drawing illustrates the new variety, with the color being as nearly true as is possible with color illustrations of this type.

DESCRIPTION OF THE PLANT

Figure 1:
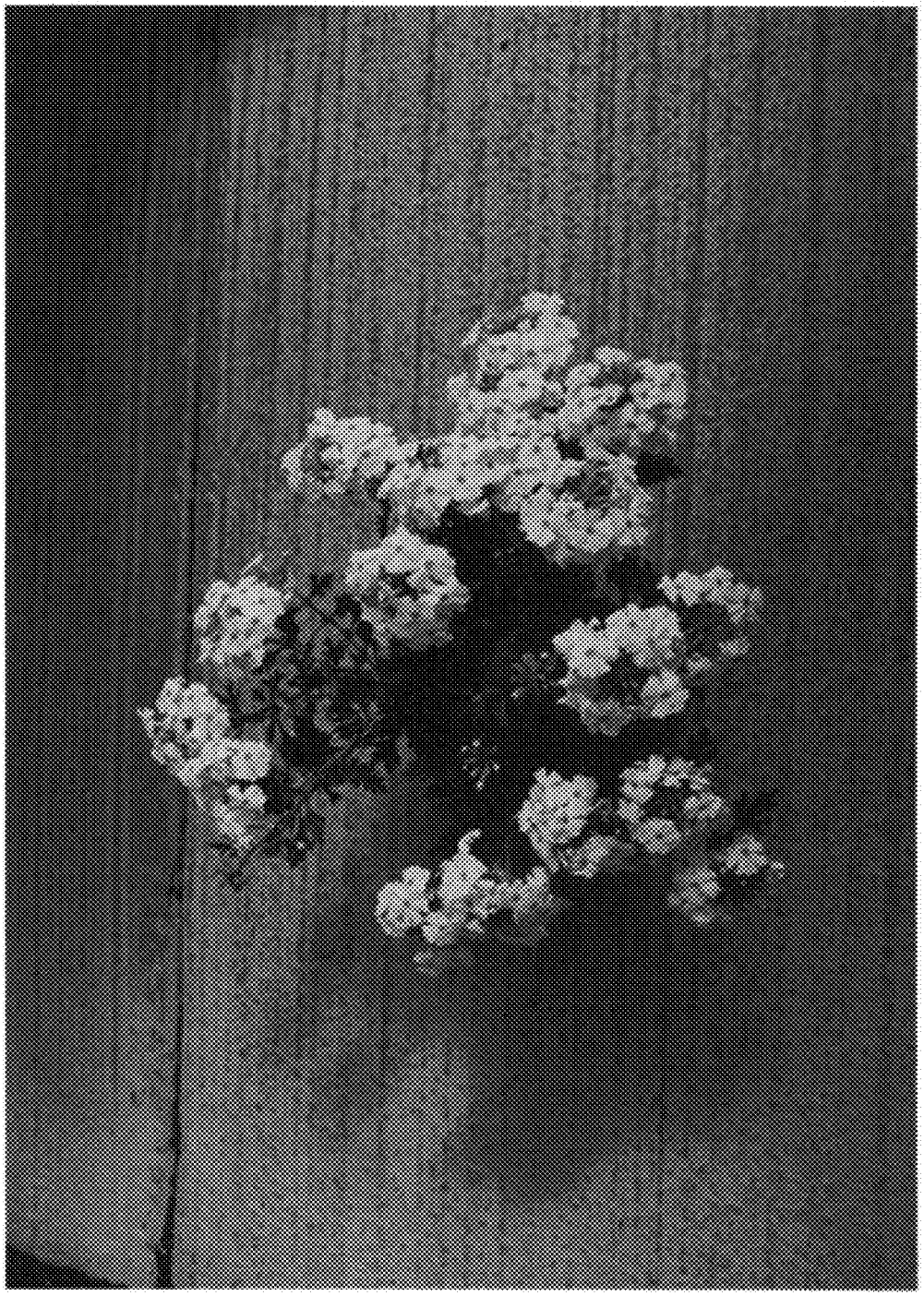
FIG. 1 is a photograph of the plant.

The following detailed description sets forth characteristics of the new cultivar. The data which defines these characteristics were collected by asexual reproductions by cuttings carried out in Waltrop, Germany. Plants for the description were 11 weeks old, grown in a greenhouse during the Summer in 10.5 cm containers. The color readings were taken in an office under artificial light. Color references are primarily to The 2001 R.H.S. Colour Chart of The Royal Horticultural Society of London.

PLANT

Form: Spreading.
Height (from soil to top of flowers): Approximately 20 cm.
Diameter: Approximately 20 cm.
Vigor: Compact.
Roots:
- *Habit.*—Spreading.
- *Time to initiate roots.*—About 10 days at 18° C.
- *Time to develop roots.*—About 21 days at 18° C.

Time to finish a flowered plant: About 10-12 weeks in a 10.5 cm container.
Branching habit: Bushy.
Lateral branches:
- *Color.*—146B.
- *Texture.*—Smooth.
- *Diameter.*—Approximately 3-4 mm.
- *Internode length.*—Approximately 20-25 mm.

Foliage:
- *Arrangement.*—Opposite.
- *Size of leaf.*—Length: 25-30 mm. Width: Approximately 18-20 mm.
- *Shape of leaf.*—Lanceolate.
- *Shape of apex.*—Acute.
- *Shape of base.*—Obtuse.
- *Texture.*—Smooth.
- *Margin.*—Crenate.
- *Color.*—Young leaves: Upper surface: 137A. Lower surface: 137D. Mature leaves: Upper surface: 137A. Lower surface: 137B.
- *Petiole.*—Length: 5 mm. Diameter: 1 mm. Color: 138B.
- *Veins.*—Venation type: Pinnate. Color: Upper surface: 138B. Lower surface: 138B.

FLOWER

Natural flowering season: From April until October.
Bud (described before opening):
*Shape.*—Long; 5 parted.
*Diameter.*—3 mm.
*Length.*—10-11 mm.
*Color.*—62C.
Spike:
*Number of flowers per spike.*—Approximately 35-45.
*Diameter.*—Approximately 15-18 mm.
*Length.*—Approximately 8-10 cm after flowering.
Corolla:
*Form.*—Fused petals.
*Petals/lobes.*—Number: 5. Length: Approximately 7-9 mm. Width: Approximately 6-7 mm. Shape: Obovate. Aspect: Flat. Margin: Lobated. Texture and appearance: Smooth. Color: When opening: Upper surface: 69B to 69C with a 71B eye. Lower surface: 69C. Fully opened: Upper surface: 69B to 69C with a 71B eye. Lower surface: 69C.
*Throat.*—Color: 130D. Texture: Smooth.
*Tube color:* 130D.
Calyx:
*Form.*—Fused at base; cylindrical.
*Length.*—Approximately 8-11 mm.
*Diameter.*—2 mm.
*Sepal.*—Shape: Cylindrical; 5 connected sepals. Margin: Acuminate. Texture: Smooth. Color: Upper surface: 137B. Lower surface: 137B to 137D.
Disease resistance: No resistance to diseases noted to date.
Fragrance: None.
Temperature tolerance: From 1° C. to 45° C.
Lasting quality: Good.

REPRODUCTIVE ORGANS

Stamens:
*Number:* 4.
*Filament length.*—0.5 mm.
*Anthers.*—Shape: Oval. Length: 0.01 mm. Color: N144D.
*Pollen.*—Color: 154C. Amount: Minimal.
Pistil:
*Length.*—10-12 mm.
*Style.*—Length: Less than 0.5 mm. Color: 137B to 137D.
*Stigma.*—Shape: Oval. Color: 137D.
Seed production: None.

I claim:

1. A new and distinct variety of *Verbena* plant named 'Gruelox 01' substantially as shown and described herein.

* * * * *